US012779134B2

(12) United States Patent
Kudo et al.

(10) Patent No.: US 12,779,134 B2
(45) Date of Patent: Nov. 3, 2026

(54) PROTECTOR-ATTACHED PUNCTURE NEEDLE

(71) Applicant: NIPRO CORPORATION, Osaka (JP)

(72) Inventors: Tatsuya Kudo, Osaka (JP); Naoki Nakagawa, Osaka (JP); Takashi Eshima, Osaka (JP)

(73) Assignee: Nipro Corporation, Osaka (JP)

(*) Notice: Subject to any disclaimer, the term of this patent is extended or adjusted under 35 U.S.C. 154(b) by 858 days.

(21) Appl. No.: 17/614,034

(22) PCT Filed: May 27, 2020

(86) PCT No.: PCT/JP2020/020965
§ 371 (c)(1),
(2) Date: Nov. 24, 2021

(87) PCT Pub. No.: WO2020/241708
PCT Pub. Date: Dec. 3, 2020

(65) Prior Publication Data

US 2022/0249783 A1 Aug. 11, 2022

(30) Foreign Application Priority Data

May 27, 2019 (JP) ................................ 2019-098777

(51) Int. Cl.

| | |
|---|---|
| ***A61M 5/32*** | (2006.01) |
| ***A61M 5/162*** | (2006.01) |
| *A61B 5/15* | (2006.01) |

(52) U.S. Cl.
CPC .......... *A61M 5/3216* (2013.01); *A61M 5/321* (2013.01); *A61B 5/150618* (2013.01);
(Continued)

(58) Field of Classification Search
CPC ........ A61M 5/3216; A61M 2005/3217; A61M 5/3204; A61M 5/3202; A61M 2005/3206;
(Continued)

(56) References Cited

U.S. PATENT DOCUMENTS 4,909,792 A * 3/1990 Norelli ................ A61M 5/3216 604/263
5,116,325 A * 5/1992 Paterson ............. A61M 5/3216 604/263
(Continued)

FOREIGN PATENT DOCUMENTS

JP H10-80486 A 3/1998
JP 2007-505722 A 3/2007
(Continued)

OTHER PUBLICATIONS

International Search Report Issued in International Patent Application No. PCT/JP2020/020965, Mailed Jun. 23, 2020 (6 pages), with English translation.
(Continued)

*Primary Examiner* — Michael J Tsai
*Assistant Examiner* — Forrest B Dipert
(74) *Attorney, Agent, or Firm* — Devlin Law Firm LLC

(57) ABSTRACT

A protector-attached puncture needle 10 in which a protector 14 is tiltably supported by a needle hub 18 of a puncture needle 12, and the protector 14 includes an accommodating groove 40 which opens toward the puncture needle 12 in a tilting direction and accommodates the puncture needle 12. Inner surfaces of both side walls 44, 44 of the accommodating groove 12 of the protector 14 include respective reinforcing ribs 52, 52 extending from a groove bottom portion toward a groove opening side. The reinforcing rib 52, 52 include respective recesses 54, 54 each opening to the inner surface of each of the side walls 44, 44. Diametrically
(Continued)

both sides of an outer peripheral portion of a cap 30 enter and are locked in the respective recesses 54, 54 of the reinforcing ribs 52, 52 such that a tilt position of the protector 14 in an unused state before removal of the cap 30 is held.

11 Claims, 4 Drawing Sheets

(52) U.S. Cl.
CPC ... *A61B 5/150664* (2013.01); *A61B 5/150671* (2013.01); *A61B 5/150687* (2013.01); *A61M 5/1626* (2013.01); *A61M 5/3202* (2013.01); *A61M 2005/3217* (2013.01)

(58) Field of Classification Search
CPC ..... A61M 2005/3247; A61B 5/150717; A61B 5/150664; A61B 5/150671; A61B 5/150679; A61B 5/150687; A61B 5/150595; A61B 5/150618
See application file for complete search history.

(56) References Cited

U.S. PATENT DOCUMENTS

| | | | | |
|---|---|---|---|---|
| 5,665,075 A * | 9/1997 | Gyure | A61M 5/3202 604/263 |
| 5,733,265 A * | 3/1998 | Bachman | A61M 5/3216 604/263 |
| 6,413,243 B1 * | 7/2002 | Geist | A61M 5/3216 604/110 |
| 8,888,713 B2 * | 11/2014 | Crawford | A61M 5/3216 600/576 |
| 2002/0193744 A1 * | 12/2002 | Alesi | A61M 5/3216 128/919 |
| 2003/0078548 A1 | 4/2003 | Kobayashi | |
| 2005/0049560 A1 * | 3/2005 | Hauri | A61M 5/3216 604/110 |
| 2008/0208138 A1 * | 8/2008 | Lim | A61M 5/3216 604/192 |
| 2013/0274684 A1 * | 10/2013 | Bubenik | A61M 5/3216 604/263 |
| 2015/0273159 A1 | 10/2015 | Zhang | |
| 2016/0015905 A1 * | 1/2016 | Fournier | A61M 5/3202 604/192 |
| 2017/0258990 A1 * | 9/2017 | Wei | A61M 5/3216 |
| 2018/0140780 A1 * | 5/2018 | Carrel | A61M 5/3216 |
| 2021/0228817 A1 * | 7/2021 | Jaber | A61M 5/46 |

FOREIGN PATENT DOCUMENTS

| | | |
|---|---|---|
| JP | 2014-527443 A | 10/2014 |
| JP | 2018-89093 A | 6/2018 |
| JP | 2018-517485 A | 7/2018 |
| WO | 2016/002389 A1 | 1/2016 |

OTHER PUBLICATIONS

Translation of International Preliminary Report on Patentability in PCT/JP2020/020965, mailed Dec. 9, 2021, 6 pages.
Office Action for Japanese Patent Application No. 2021-522829, issued Nov. 27, 2023, Japanese and English translation (9 pages).
Office Action for Japanese Patent Application No. 2024-061234, issued Jan. 8, 2025, Japanese and English translations (7 pages).

* cited by examiner

PROTECTOR-ATTACHED PUNCTURE NEEDLE

CROSS-REFERENCE TO RELATED APPLICATIONS

This application is a U.S. National Stage of International Application No. PCT/JP2020/020965, filed on May 27, 2020, and claims priority under 35 U.S.C. § 119 to Japanese Application No. JP 2019-098777, filed on May 27, 2019, the contents of which are incorporated by reference herein in their entirety.

TECHNICAL FIELD

The present invention relates to a protector-attached puncture needle provided with a protector that protects the puncture needle after use of the puncture needle that is stuck into a blood vessel.

BACKGROUND ART

Conventionally, a puncture needle provided with a protector that protects the puncture needle after use has been known for the purpose of preventing erroneous puncture and reuse, facilitating disposal, and the like. A puncture needle provided with such a protector is proposed, for example, in International Publication No. WO 2016/002389 (Patent Document 1).

Meanwhile, the protector-attached puncture needle described in Patent Document 1 includes a protector (a sheath 20 in Patent Document 1) that protects the puncture needle after use, and a cap that protects the puncture needle before use (a protector 18 in Patent Document 1).

BACKGROUND ART DOCUMENTS

Patent Documents

Patent Document 1: WO 2016/002389

SUMMARY OF THE INVENTION

Problem the Invention Attempts to Solve

However, the protector-attached puncture needle described in Patent Document 1 is not provided with a positioning mechanism of the protector before use. Therefore, there is a possibility that the protector may be displaced so as to protrude outward during transportation, packing or the like, which may hinder the work of transportation, packing or the like.

Further, when using the protector-attached puncture needle described in Patent Document 1, a complicated operation of separating the protector from the cap in the tilting direction and then removing the cap is required, and improvement in operability is required.

It is an object of the present invention to provide a protector-attached puncture needle with a novel structure which is able to eliminate any one of the problems inherent in the protector-attached puncture needle having a conventional structure, such as being able to prevent the protector from protruding greatly outward before use and improving operability.

Means for Solving the Problem

Hereinafter, preferred embodiments for grasping the present invention will be described. However, each preferred embodiment described below is exemplary and can be appropriately combined with each other. Besides, a plurality of elements described in each preferred embodiment can be recognized and adopted as independently as possible, or can also be appropriately combined with any element described in other preferred embodiments. By so doing, in the present invention, various other preferred embodiments can be realized without being limited to those described below.

A first preferred embodiment provides a protector-attached puncture needle comprising: a puncture needle; a cap removably covering the puncture needle before use; and a protector configured to cover the puncture needle after use, wherein the protector is tiltably supported by a needle hub of the puncture needle, and the protector includes an accommodating groove that opens toward the puncture needle in a tilting direction to accommodate the puncture needle, inner surfaces of both side walls of the accommodating groove of the protector include respective reinforcing ribs extending from a groove bottom portion toward a groove opening side, and the reinforcing ribs include respective recesses each opening to the inner surface of the corresponding side wall, and diametrically both sides of an outer peripheral portion of the cap enter and are locked in the respective recesses of the reinforcing ribs such that a tilt position of the protector in an unused state before removal of the cap is held.

According to the protector-attached puncture needle of the present preferred embodiment, the tilt position of the protector can be held and the protector can be prevented from being accidentally displaced before use when the cap is not removed. This makes it possible to prevent the protector from protruding outward greatly in the state before use, thereby facilitating operations such as transportation and packaging.

Further, by simply providing a reinforcing rib on the inner surface of the side wall of the protector to suppress collapse deformation or the like of the side wall, indeed, the reinforcing rib and the outer peripheral portion of the cap come into contact with each other, and the side wall of the protector expands outward, posing a risk or the like of hindering the protection of the puncture needle by the protector after use due to the side wall of the protector being provided with a peculiarity spreading outward. Here, in the present embodiment, a recess is provided on the inner surface of the side wall so that the outer peripheral portion of the cap enters the said recess, thereby reducing the pressing force of the outer peripheral portion of the cap on the side wall outward in the direction of opposition, while realizing the function of holding the tilt position of the cap before use by skillfully using the reinforcing ribs. Therefore, for example, even when stored for a long period of time, attachment of a peculiarity of deforming the side wall or the like is avoided.

A second preferred embodiment provides the protector-attached puncture according to the first preferred embodiment, wherein each recess is constituted by a through hole that penetrates the corresponding side wall of the accommodating groove in a thickness direction.

According to the protector-attached puncture needle of the present preferred embodiment, since the cap is visually recognized from the outside through the through hole, it is possible to easily determine that the cap and the protector are in the locked state.

A third preferred embodiment provides the protector-attached puncture needle according to the first or second preferred embodiment, wherein the protector includes second reinforcing ribs positioned on a distal end side with respect to the reinforcing ribs and extending from the groove bottom portion toward the groove opening side on the respective inner surfaces of the side walls of the accommodating groove, and an end of each second reinforcing rib on the groove opening side is in contact with the outer peripheral portion of the cap such that in the unused state before removal of the cap, tilt of the protector in a direction approaching the puncture needle is limited.

According to the protector-attached puncture needle of the present preferred embodiment, the reinforcing effect of the protector is improved by the second reinforcing rib. Besides, in addition to the tilt position holding effect of the protector by the recess provided in the reinforcing rib, the tilt limiting effect of the protector by the second reinforcing rib can more reliably prevent the displacement of the protector in the unused state.

A fourth preferred embodiment provides a protector-attached puncture needle comprising: a puncture needle; a cap removably covering the puncture needle before use; and a protector configured to cover the puncture needle after use, wherein the protector is tiltably supported by a needle hub of the puncture needle, and the protector includes an accommodating groove that opens toward the puncture needle in a tilting direction to accommodate the puncture needle, both side walls of the accommodating groove of the protector include respective through holes each opening on inner and outer surfaces of the corresponding side wall, and diametrically both sides of an outer peripheral portion of the cap, the cap being inserted in the accommodating groove, enter and are locked in respective openings of the through holes to the accommodating groove such that a tilt position of the protector in an unused state before removal of the cap is held.

According to the protector-attached puncture needle of the present preferred embodiment, the tilt position of the protector can be held and the protector can be prevented from being accidentally displaced before use when the cap is not removed. This makes it possible to prevent the protector from protruding outward greatly in the state before use, thereby facilitating operations such as transportation and packaging.

In particular, by skillfully utilizing the relationship between the through hole provided in the side wall of the protector and the outer peripheral shape of the cap that is convex outward, the protector can be held at a specific tilt position before use with a simple structure. That is, the through hole for holding the cap can be easily formed by molding, and a corner portion can be easily formed at the opening edge of the through hole, so that the cap and the protector can be locked more stably. Further, it can be easily determined whether or not the cap and the protector are in the locked state through the through hole.

A fifth preferred embodiment provides a protector-attached puncture needle comprising: a puncture needle; a cap removably covering the puncture needle before use; and a protector configured to cover the puncture needle after use, wherein the protector is tiltably supported by a needle hub of the puncture needle, and the protector includes an accommodating groove that opens toward the puncture needle in a tilting direction to accommodate the puncture needle, inner surfaces of both side walls of the accommodating groove of the protector include respective first positioning protrusions and respective second positioning protrusions that are separated from each other in the tilting direction of the protector, and diametrically both sides of an outer peripheral portion of the cap, the cap being inserted in the accommodating groove, are positioned between the respective first positioning protrusions and the respective second positioning protrusions such that a tilt position of the protector in an unused state before removal of the cap is held in a state in which an expanding force is not exerted on the accommodating groove, the expanding force being caused by contact reaction force of the side walls of the accommodating groove of the protector with respect to the diametrically both sides of the outer peripheral portion of the cap inserted in the accommodating groove.

According to the protector-attached puncture needle of the present preferred embodiment, the tilt position of the protector can be held and the protector can be prevented from being accidentally displaced before use when the cap is not removed. This makes it possible to prevent the protector from protruding outward greatly in the state before use, thereby facilitating operations such as transportation and packaging.

In particular, in a state in which the tilt position of the protector is held before use, the action of the expanding force on the side wall of the accommodating groove is avoided, so that the side wall is prevented from being provided with a peculiarity of strange shape even when stored for a long period of time, for example, thereby being held in a predetermined shape set in advance. Therefore, for example, when the cap is removed and the puncture needle is protected by the protector etc. as well, the protective effect of the puncture needle by the protector can be obtained more stably or the like. In particular, in a configuration in which both side walls are involved in the protective action of the puncture needle by the protector, the protective effect of the puncture needle by the protector can be obtained more stably.

A sixth preferred embodiment provides the protector-attached puncture needle according to any of the first through fifth preferred embodiments, wherein the outer peripheral portion of the cap inserted in the accommodating groove of the protector has a cylindrical shape.

According to the protector-attached puncture needle of the present preferred embodiment, it is not necessary to align the cap and the protector in the circumferential direction, so that the tilt position of the protector can be held regardless of the circumferential position of the cap.

A seventh preferred embodiment provides the protector-attached puncture needle according to any of the first to sixth preferred embodiments, wherein the protector includes a pair of contact portions that are in contact with the outer peripheral portion of the cap, the contact portions extending parallel to a center axis of the cap while being separated from each other in the tilting direction at the tilt position of the protector in the unused state before removal of the cap, and the outer peripheral portion of the cap enters between the contact portions such that the tilt position of the protector is held.

According to the protector-attached puncture needle of the present preferred embodiment, the cap and the protector can be brought into an approximately linear contact with each other. Thus, in comparison with the case where the cap and the protector are brought into point contact with each other, for example, larger length dimensions of the contact portions between the cap and the protector can be secured, thereby improving the force of holding the protector at the tilt position or the like.

An eighth preferred embodiment provides the protector-attached puncture needle according to any of the first to seventh preferred embodiments, further comprising a positioning mechanism positioning the tilt position of the protector separately at a puncture position away from the puncture needle and at a protection position where the puncture needle is covered.

According to the protector-attached puncture needle of the present preferred embodiment, the puncture position and the protection position of the protector can be set more stably to a specific position in consideration of the desired functions or the like such as compact performance in the stored state and hindrance avoiding performance with respect to the operations during puncture.

A ninth preferred embodiment provides a protector-attached puncture needle comprising: a puncture needle; a cap covering the puncture needle before use and capable of being pulled out; and a protector being tiltable and configured to cover the puncture needle from a lateral side after use, wherein the cap includes a contact protrusion configured to come into contact with the protector when the cap is pulled out, the protector being held at a tilt position approaching the cap before use, and the protector is configured to be tilted to a tilt position away from the cap by the contact protrusion coming into contact with the cap and exerting a pulling out force due to pulling out of the cap.

According to the protector-attached puncture needle of the present preferred embodiment, the protector held in an approaching position to the cap before use can be almost automatically tilted to the puncture position away from the cap by simply pulling out the cap when used. Therefore, for example, the practitioner does not need to perform the cumbersome work of two steps of tilting the protector and then removing the cap during use, which improves operability and enables quick treatment.

A tenth preferred embodiment provides the protector-attached puncture needle according to the ninth preferred embodiment, wherein the protector is connected to a needle hub of the puncture needle by an elastic hinge by which a puncture position away from the puncture needle is set as a stable position.

According to the protector-attached puncture needle of the present preferred embodiment, before use, the elastic hinge is elastically deformed to hold the protector in a tilt position approaching the cap, and during use, by removing the cap, the protector can be automatically displaced to a stable position (the puncture position) away from the puncture needle in accordance with the elastic recovering deformation of the elastic hinge. The elastic hinge in the present preferred embodiment may have a stable position only at the puncture position, or may have another stable position at a position other than the puncture position.

An eleventh preferred embodiment provides the protector-attached puncture needle according to the ninth or tenth preferred embodiment, wherein the contact protrusion of the cap is constituted by a flange-shaped portion projecting on an outer peripheral surface on a proximal end side of the cap.

According to the protector-attached puncture needle of the present preferred embodiment, it is possible to eliminate the need for alignment of the cap in the circumferential direction, and it is also possible to improve the strength of the proximal end side of the cap by utilizing the contact protrusion.

A twelfth preferred embodiment provides the protector-attached puncture needle according to any of the ninth to eleventh preferred embodiments, wherein the protector includes an accommodating groove configured to accommodate and cover the puncture needle from the lateral side after use, and an engaging protrusion projects on at least one of inner surfaces of side walls of the accommodating groove, the engaging protrusion being configured to be contacted by the contact protrusion due to pulling out of the cap.

According to the protector-attached puncture needle of the present preferred embodiment, the engaging protrusion with which the contact protrusion comes into contact is formed so as to project on the inner surface of the accommodating groove of the protector. With this configuration, as compared with the case where the contact protrusion is brought into contact with the end face on the proximal end side of the accommodating groove of the protector or the like, for example, the contact position of the contact protrusion can be appropriately set regardless of the outer shape of the protector or the like.

A thirteenth preferred embodiment provides the protector-attached puncture needle according to the twelfth preferred embodiment, wherein at the position approaching the cap where the protector is held before use, the engaging protrusion of the protector extends toward an opening side of the accommodating groove beyond a contact position with the contact protrusion due to pulling out of the cap, and even after the cap starts to move due to pulling out operation and the protector starts to tilt, the contact protrusion is configured to be in contact with the engaging protrusion in a moving region having a predetermined length in a pulling out direction of the cap.

According to the protector-attached puncture needle of the present preferred embodiment, even when the contact position of the contact protrusion with respect to the protector changes as the tilt of the protector progresses due to the pulling out of the cap, the contact state of the contact protrusion with the protector is maintained, whereby the tilting force exerted on the protector based on the contact can be maintained. In short, it is possible to continuously apply the tilting force exerted on the protector when pulling out the cap not only in a single position but also over a predetermined movement position, and as a result, the protector can be more reliably tilted. It is acceptable as long as the engaging protrusion of the protector in the present preferred embodiment is provided so as to extend toward the opening side of the accommodating groove beyond the contact position with the contact protrusion due to the pulling out the cap. The engaging protrusion does not necessarily extend in a continuous fashion, but may be provided so as to intermittently extend such that the engaging protrusion intermittently comes into contact with the contact protrusion as the pulling out of the cap progresses.

Effect of the Invention

The protector-attached puncture needle according to the present invention makes it possible to achieve at least one of the novel effects which were not realized by the conventional protector-attached puncture needle, such as being able to stably hold the tilt position of the protector in the unused state to prevent the protector from protruding greatly outward, and being able to guide the protector to the tilt position away from the puncture needle to improve workability.

EMBODIMENTS FOR CARRYING OUT THE INVENTION

Hereinafter, in order to clarify the present invention in more detail, practical embodiments of the present invention will be described in detail with reference to the drawings.

Figure 1:
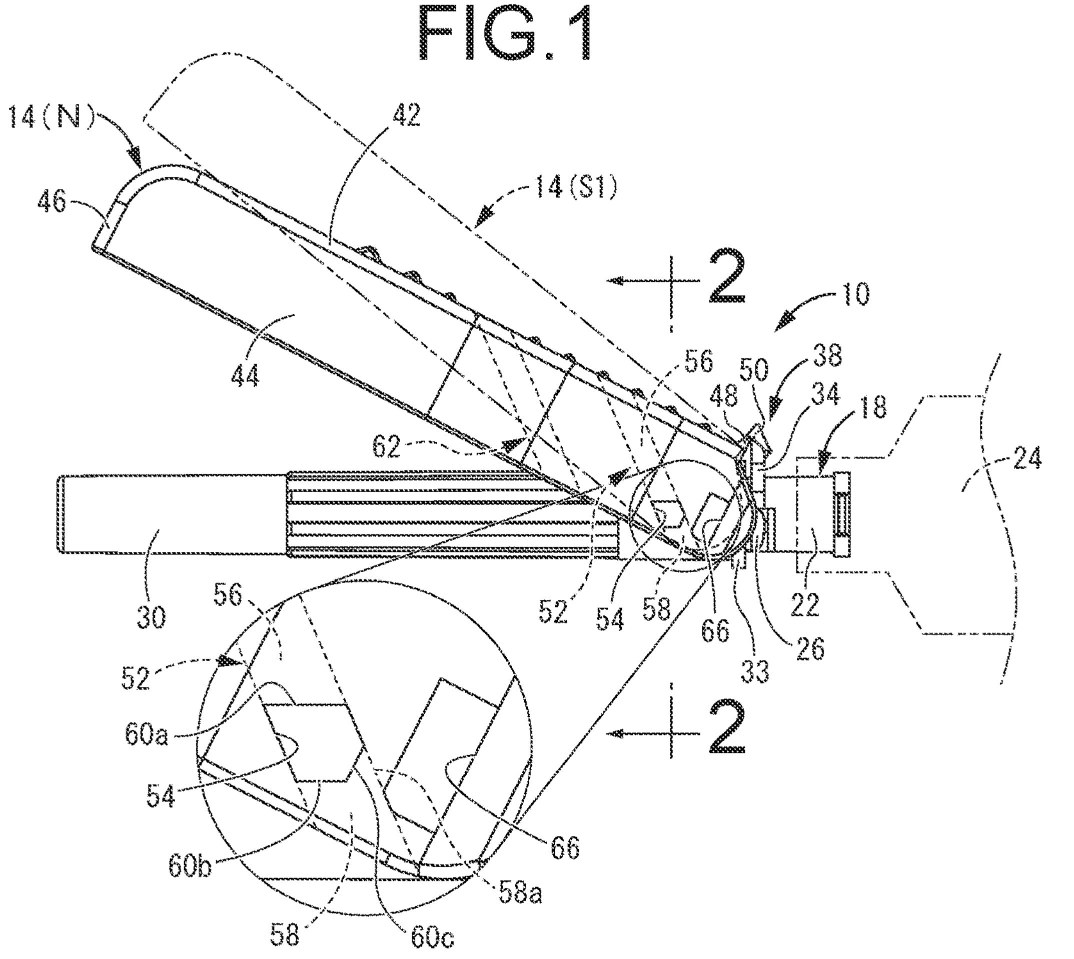
FIG. 1 is a front view showing a protector-attached puncture needle as a first practical embodiment of the present invention, with a tilt state of a protector held in an unused state.
Figure 2:
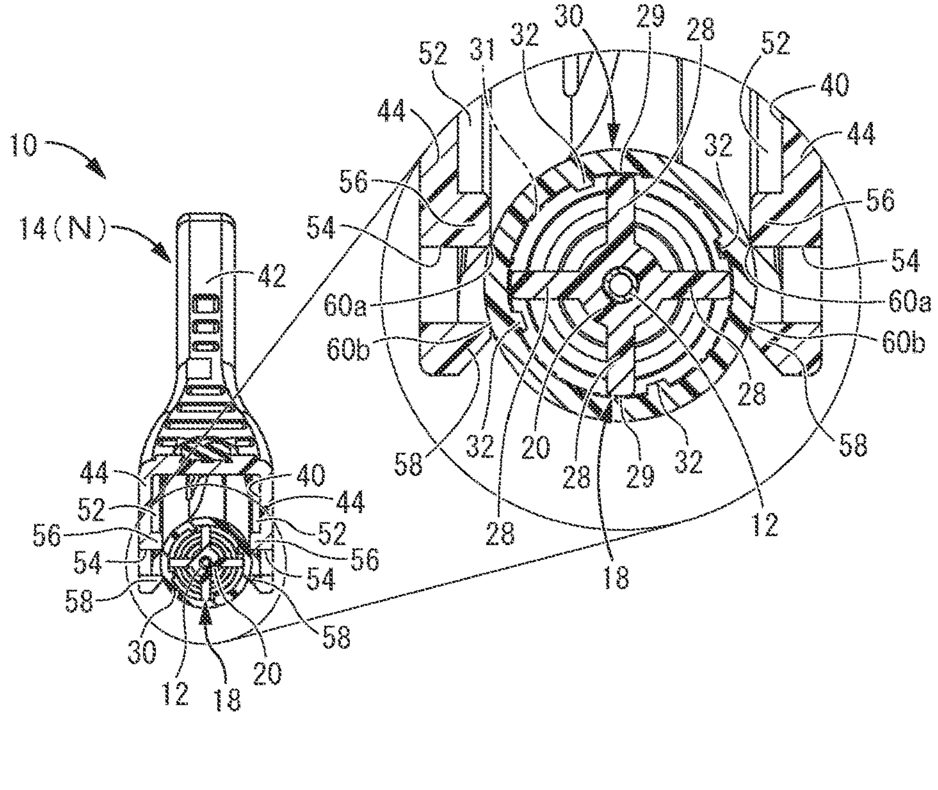
FIG. 2 is a cross sectional view taken along line 2-2 of FIG. 1.

First, FIGS. 1 and 2 show a protector-attached puncture needle 10 as a first practical embodiment of the present invention in an unused state before use. The protector-attached puncture needle 10 includes a puncture needle 12 that punctures a blood vessel and a protector 14 that protects the puncture needle 12 after puncture. In the following description, the axial direction refers to the left-right direction in FIG. 1, which is the center axis direction of the puncture needle 12. The distal end side refers to the left side in FIG. 1 which is the needle tip 16 (see FIG. 4) side of the puncture needle 12, and the proximal end side refers to the right side in FIG. 1.

More specifically, the proximal end of the puncture needle 12 is fixed to a needle hub 18. The puncture needle 12 is a hollow needle made of stainless steel, titanium, or the like, and has a sharp needle tip 16.

Figure 4:
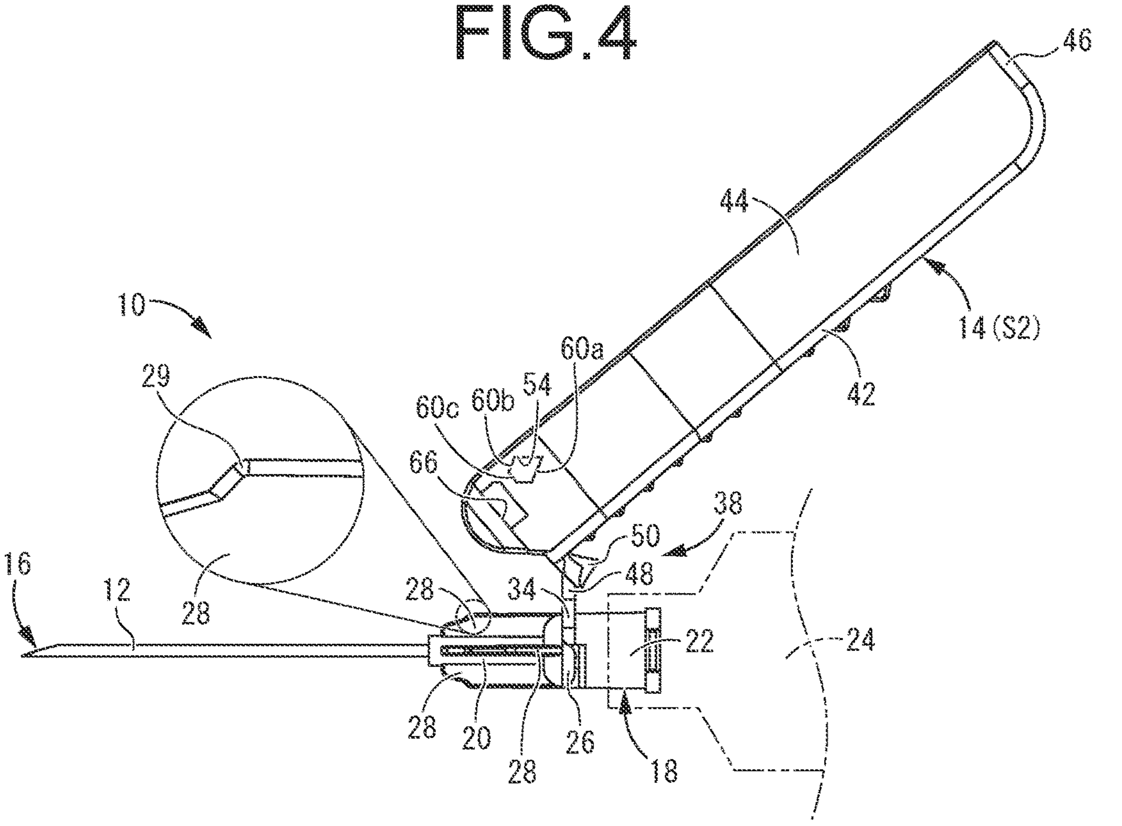
FIG. 4 is a front view showing a state in which the cap is pulled out and the protector is displaced to a puncture position in the protector-attached puncture needle shown in FIG. 1.
Figure 5:
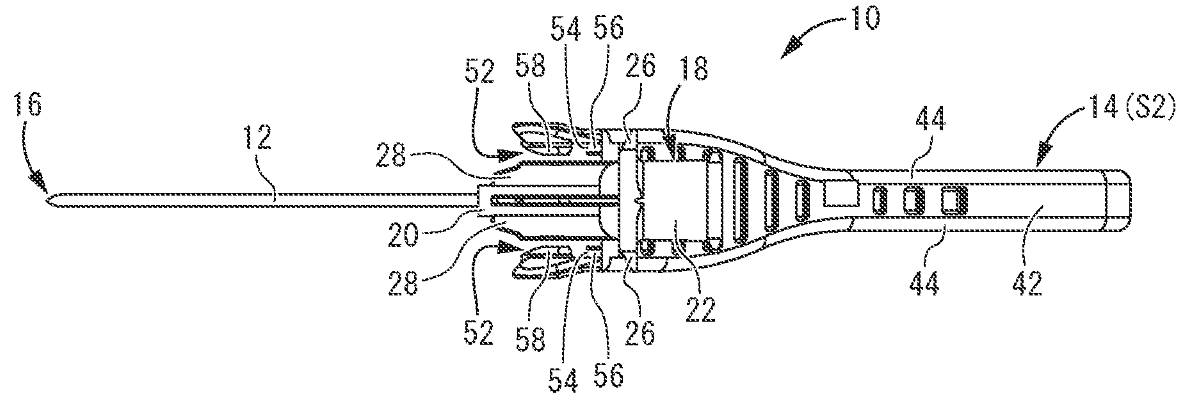
FIG. 5 is a bottom plan view of the protector-attached puncture needle shown in FIG. 4.

As shown in FIGS. 4 and 5 described later, the needle hub 18 has an approximately stepped tubular shape extending in the axial direction overall, and is formed of a rigid synthetic resin or the like. The needle hub 18 includes a small-diameter tubular portion 20 on the distal end side and a large-diameter tubular portion 22 on the proximal end side.

The puncture needle 12 is fixed to the needle hub 18 by inserting the proximal end portion of the puncture needle 12 into the small-diameter tubular portion 20 and adhering or welding the puncture needle 12 as needed. Alternatively, the puncture needle 12 and the needle hub 18 can be integrally formed by molding the needle hub 18 with the puncture needle 12 set inside the cavity.

Further, a syringe 24 or the like in which the drug solution is sealed can be connected to the proximal end side of the large-diameter tubular portion 22, and the drug solution in the syringe 24 can be injected into the blood vessel of the patient through the puncture needle 12.

In the present practical embodiment, an approximately plate-shaped locking protrusion 26 projecting to the outer peripheral side is integrally molded at the distal end portion of the large-diameter tubular portion 22. In particular, in the present practical embodiment, the pair of locking protrusions 26, 26 project in the opposite directions to each other in the diametrical direction (the vertical direction in FIG. 5 described later).

Fixing plate portions 28 projecting to the outer peripheral side are provided on the outer peripheral surface of the small-diameter tubular portion 20. In this practical embodiment, four fixing plate portions 28 are provided at approximately equal intervals in the circumferential direction. In particular, in the present practical embodiment, a stepped portion is provided at the distal end portion of the fixing plate portion 28, and as shown in an enlarged view of the stepped portion in FIG. 4 described later, in the fixing plate portion 28, the protrusion dimension to the outer peripheral side is slightly increased from the proximal end side toward the stepped portion, while the protrusion dimension to the outer peripheral side is decreased on the distal end side of the stepped portion. Accordingly, the fixing plate portion 28 is provided with a maximum protruding portion 29 having the largest protrusion dimension to the outer peripheral side in the stepped portion.

In the unused state shown in FIGS. 1 and 2, the puncture needle 12 is protected by a cap 30. The cap 30 has an approximately bottomed cylindrical shape that opens toward the proximal end side overall, and is formed of a rigid synthetic resin or the like. By inserting the small-diameter tubular portion 20 including the fixing plate portion 28 into the opening of the cap 30 by press fitting or the like, the cap 30 is removably attached to the needle hub 18 while covering the puncture needle 12.

In the present practical embodiment, as indicated by the chain double-dashed line in the enlarged view of FIG. 2, the inner circumferential surface of the opening portion on the proximal end side of the cap 30 is provided with an approximately annular surmountable protrusion 31 protruding radially inward. The cap 30 is press-fitted into the needle hub 18, and the maximum protruding portion 29 of the fixing plate portion 28 climbs over and engages with the surmountable protrusion 31, so that the cap 30 is removably attached to the needle hub 18. Further, a plurality of ridges 32 extending in the axial direction are provided on the inner circumferential surface of the opening portion on the proximal end side of the cap 30, and by the ridges 32 and the fixing plate portions 28 being brought into contact with each other in the circumferential direction, relative rotation of the needle hub 18 and the cap 30 is prevented. Further, the opening portion on the proximal end side of the cap 30 is provided with a contact protrusion projecting to the outer peripheral side, and in the present practical embodiment, the contact protrusion is a flange-shaped portion 33 extending continuously over the entire circumference in the circumferential direction.

Here, the needle hub 18 is provided with the protector 14, and in the present practical embodiment, the protector 14 is integrally molded with the needle hub 18. In particular, in the present practical embodiment, an approximately plate-shaped connecting portion 34 projecting from the distal end portion of the needle hub 18 to the outer peripheral side and the protector 14 are connected to each other by a hinge portion 38. As a result, the protector 14 is tiltably supported by the hinge portion 38 with respect to the needle hub 18. In the unused state shown in FIGS. 1 and 2, the protector 14 extends so as to tilt with respect to the axial direction, as will be described later.

The protector 14 has an accommodating groove 40 in which the groove length dimension is larger than the groove width dimension. Then, by the protector 14 tilting with respect to the needle hub 18, and the puncture needle 12 being accommodated in the accommodating groove 40, the puncture needle 12 is protected by the protector 14.

That is, the accommodating groove 40 includes a bottom wall 42 extending in the groove length direction and a pair of side walls 44, 44 protruding toward the puncture needle 12 side from both ends in the width direction (the left-right direction in FIG. 2) of the bottom wall 42, and opens toward the puncture needle 12 in the tilting direction. The distal end side of the accommodating groove 40 is closed by a distal end side wall 46. In the present practical embodiment, the side walls 44, 44 are curved at the middle portion in the length direction, and the distance between the opposed faces of the side walls 44, 44 varies in the length direction of the side wall 44. Accordingly, the distance between the opposed faces of the side walls 44, 44 (the groove width dimension of the accommodating groove 40) is made smaller on the distal end side, and is made larger on the proximal end side.

The structure of the hinge portion 38 is not limited, but in the present practical embodiment, the hinge portion 38 is constituted by a spring hinge. That is, the hinge portion 38 includes a pair of connecting arms 48, 48 that can be bent in association with the tilting of the protector 14 and an urging arm 50 serving as an elastic hinge that is located between the connecting arms 48, 48 and provides the protector 14 with an urging force for tilting. One lengthwise end of the connecting arms 48, 48 and the urging arm 50 is connected to the proximal end (the end on the side closer to the hinge portion 38) of the bottom wall 42 of the protector 14, while the other lengthwise end of the connecting arms 48, 48 and the urging arm 50 is connected to the protruding end of the connecting portion 34 toward the outer peripheral side.

The connecting arm 48 has a structure in which a thin-walled portion is formed in the middle portion in the length direction of the plate-shaped member, and can be bent around the thin-walled portion. Further, the urging arm 50 is constitute by an elastic piece to which elasticity is given by being bent or curved at the middle portion in the length direction of a plate-shaped member. Then, the protector 14 undergoes tilt displacement to elastically deform the urging arm 50, so that the protector 14 is positioned by selecting its position from a plurality of stable positions in a multiple-choice manner.

Here, on the inner surface of the side wall 44 of the protector 14, a reinforcing rib 52 serving as an engaging protrusion extending from the groove bottom portion (the bottom wall 42) toward the groove opening side is formed, and in the present practical embodiment, respective reinforcing ribs (engaging ribs) 52, 52 are provided on the inner surfaces of both side walls 44, 44. In particular, in the present practical embodiment, the reinforcing ribs 52, 52 are provided at the proximal end portions of the respective side walls 44, 44 while extending so as to be inclined with respect to the length direction of the protector 14, and are formed over the entire length from the groove bottom portion up to the groove opening. These reinforcing ribs 52, 52 have a certain width dimension and a certain protrusion dimension from the side wall 44, 44, and the width dimension and the protrusion dimension are approximately constant over the entire length.

A recess that opens to the inner surface of the side wall 44 is provided in the middle portion of each reinforcing rib 52 in the length direction. In the present practical embodiment, the recess is formed by a through hole 54 that penetrates the side wall 44 in the thickness direction. That is, the through hole 54 opens on the inner and outer surfaces of the side wall 44, and the inner opening is provided in the accommodating groove 40. Such a through hole 54 can be formed by molding (for example, injection molding), whereby in the present practical embodiment, the opening edge of the through hole 54 is formed by a corner portion of approximately 90 degrees.

The through hole 54 is formed over the entire length of the reinforcing rib 52 in the width direction, and the reinforcing rib 52 is divided into an upper rib 56 on the upper side in FIG. 1 and a lower rib 58 on the lower side in FIG. 1. In the present practical embodiment, in the unused state shown in FIGS. 1 and 2, the upper edge (the lower edge of the upper rib 56) 60*a* of the through hole 54 extends approximately parallel to the axial direction (the center axis direction of the cap 30) with a certain length dimension. Further, the distal end side portion of the lower edge of the through hole 54 (the upper edge of the lower rib 58) constitutes a parallel portion 60*b* extending approximately parallel to the axial direction (the center axis direction of the cap 30), that is, approximately parallel to the upper edge 60*a* of the through hole 54 with a certain length dimension. The proximal end side portion of the lower edge of the through hole 54 constitutes an inclined portion 60*c* that inclines upward toward the proximal end side, and by securing a certain amount of dimension between the through hole 54 and a locking hole 66 described later, the strength of the said portion can be surely obtained.

In the present practical embodiment, on the inner surfaces of the side walls 44, 44 of the protector 14, second reinforcing ribs 62, 62 extending from the groove bottom portion toward the groove opening side are formed on the distal end side with respect to the reinforcing ribs 52, 52. Each second reinforcing rib 62 extends so as to be inclined with respect to the length direction of the protector 14, and is formed over the entire length from the groove bottom portion up to the groove opening side. In this practical embodiment, each second reinforcing rib 62 extends approximately parallel to the reinforcing rib 52. Further, the width dimension and the protrusion dimension of each second reinforcing rib 62 are not limited, but for example, the width dimension and the protrusion dimension may be gradually increased from the groove bottom portion to the groove opening side.

Figure 7:
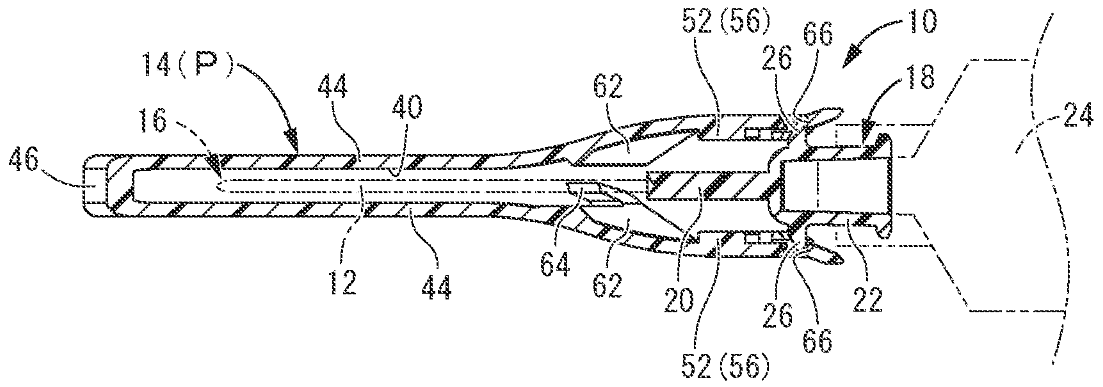
FIG. 7 is a cross sectional view taken along line 7-7 of FIG. 6.

Further, at the end on the groove opening side of the second reinforcing rib 62 on one side (the lower side in FIG. 7 to be described later), a locking portion 64 is provided so as to fold back toward the groove bottom portion side. Furthermore, locking holes 66, 66 penetrating in the thickness direction are formed at the proximal end portions of the side walls 44, 44.

The protector-attached puncture needle 10 of the present practical embodiment as described above is configured such that the protector 14 is held, by the cap 30, at a tilt position approaching the cap 30 in the unused state shown in FIGS. 1 and 2. The tilt position of the protector 14 in the unused state is shown in FIG. 1 as (N), and in FIG. 1, the state in which the protector 14 is positioned in the first stable position (S1) where the protector 14 approaches the puncture needle 12 due to elastic deformation of the urging arm 50, for example, is indicated by an imaginary line. The first stable position (S1) of the protector 14 shown in FIG. 1 is merely an example and is not limited, but for example, the length direction of the protector 14 in the first stable position (S1) tilts with respect to the axial direction, and the tilt angle is set within the range of 30 degrees to 50 degrees. However, the first stable position (S1) is not limited to the mode set by the urging arm 50. For example, the first stable position (S1) may be defined by the state in which the opening edge of the accommodating groove 40 (the end of the side wall 44 opposite to the bottom wall 42) and the outer peripheral surface of the cap 30 are in contact with each other.

In the first stable position (S1), the protector 14 is pressed toward the puncture needle 12 from the state in which the opening edge of the accommodating groove 40 and the outer peripheral surface of the cap 30 are separated from each other, whereby the opening edge of the accommodating groove 40 and the outer peripheral surface of the cap 30 comes into contact with each other. If the opening edge of the accommodating groove 40 and the outer peripheral surface of the cap 30 are already in contact with each other at the first stable position (S1), this operation is not necessary.

Further, by pressing the protector 14 toward the puncture needle 12, the opening edge of the accommodating groove 40 is elastically deformed so as to expand outward in the groove width direction (both sides in the left-right direction in FIG. 2), and the cap 30 is inserted into the accommodating groove 40 (the pair of side walls 44, 44). Then, when diametrically both sides of the outer peripheral portion of the cap 30 climb over the lower ribs 58, 58 and come into contact with the upper ribs 56, 56, the lower ribs 58, 58 (the opening edge of the accommodating groove 40) undergo recovering deformation in an elastic manner.

Here, the diameter of the cap 30 is slightly larger than the distance between the opposed faces of the reinforcing ribs 52, 52 (the distance in the left-right direction in FIG. 2), and diametrically both side portions of the outer peripheral portion of the cap 30 (the portion having the largest diametrical dimension in the cap 30) enter and are locked in the openings of the through holes 54, 54 to the accommodating groove 40. In other words, diametrically both sides of the outer peripheral portion of the cap 30 are sandwiched and positioned between the respective upper ribs 56, 56 and the respective lower ribs 58, 58, which are separated from each other in the tilting direction of the protector 14. Therefore, in the present practical embodiment, first positioning protrusions and second positioning protrusions that position diametrically both sides of the outer peripheral portion of the cap 30 are respectively constituted by the upper ribs 56, 56 and the lower ribs 58, 58.

With this configuration, the protector 14 that was in the first stable position (S1) can be held in the tilt position (N) in the unused state, and the protector 14 can be positioned with a larger holding force as compared with the state in which the protector 14 is simply positioned by the urging arm 50 (the hinge portion 38). As a result, the tilt angle of the length direction of the protector 14 with respect to the axial direction is smaller in the tilt position (N) in the unused state than in the first stable position (S1), and is set within the range of, for example, 20 degrees to 40 degrees.

In this positioned state, the lower ribs 58, 58 have undergone recovering deformation to an approximately initial position (the position of the protector 14 in its single state in which the cap 30 is not locked), and the contact reaction force due to contact with the cap 30 is approximately prevented from being exerted on the side walls 44, 44. That is, it is possible to avoid exerting an expanding force on the accommodating groove 40 due to the contact reaction force caused by the contact with the cap 30.

Then, the opening edge in the accommodating groove 40 of the through hole 54, 54, particularly the upper edge 60*a* of the through hole 54, 54 and the parallel portion 60*b* of the lower edge thereof extends approximately parallel to the axial direction and is in contact with the outer peripheral surface of the cap 30, thereby holding the tilt position of the protector 14. That is, in the present practical embodiment, contact portions of the protector 14 that are in contact with the outer peripheral portion of the cap 30 are constituted by the upper edge (the lower edge of the upper rib 56) 60*a* of the through hole 54 and the parallel portion 60*b* of the lower edge (the upper edge of the lower rib 58) of the through hole 54. In other words, the tilt position of the protector 14 is held by the outer peripheral portion of the cap 30 entering between the pair of contact portions (the upper edge 60*a* and the parallel portion 60*b*). As a result, the protector 14 is prevented from being accidentally displaced with respect to the cap 30 in the directions of approaching and separating from the puncture needle 12.

In the present practical embodiment, in a state in which the tilt position (N) of the protector 14 is held when not in use as described above, the end of the second reinforcing rib 62 on the groove opening side is in contact with the outer peripheral portion of the cap 30. With this configuration, the tilt displacement of the protector 14 in the direction approaching the puncture needle 12 can be more reliably prevented.

Figure 3:
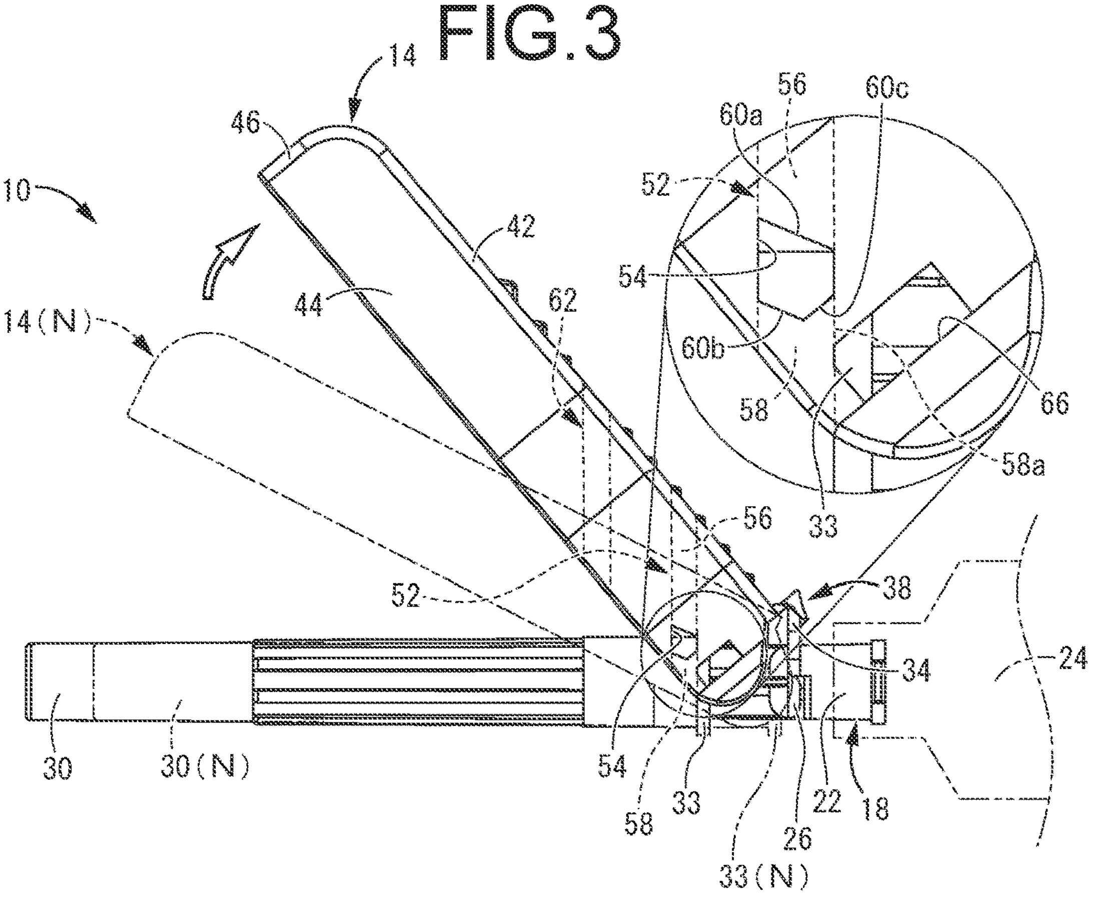
FIG. 3 is a front view showing a state in which a cap is being pulled out and removed from the protector-attached puncture needle shown in FIG. 1, with a contact protrusion and an engaging protrusion engaged with each other.

When using such an unused protector-attached puncture needle 10, after connecting the syringe 24 or the like to the needle hub 18 of the protector-attached puncture needle 10 housed in the packaging material in the unused state, the protector-attached puncture needle 10 is taken out of the packaging material. Then, the cap 30 is pulled out from the protector-attached puncture needle 10 outward in the axial direction (leftward in FIG. 3) to remove the cap 30. FIG. 3 shows the protector-attached puncture needle 10 in the state in which the cap 30 is being removed, and shows the protector 14 and the cap 30 in the tilt position (N) in the unused state by the chain double-dashed line.

In the unused state, the reinforcing rib 52 inclines with respect to the pulling out direction (the axial direction) of the cap 30. By pulling the cap 30 outward in the axial direction (namely, moving the cap 30 to the distal end side with respect to the protector 14), the flange-shaped portion 33 provided in the proximal end side opening portion of the cap 30 comes into contact and engages with the proximal end side end face 58*a* of the lower rib 58 of the reinforcing rib 52. Then, by further pulling out the cap 30 in a state in which the flange-shaped portion 33 and the lower rib 58 are engaged, the protector 14 is subjected to an external force in the tilting direction so as to rotate about the contact portion by the proximal end side end face 58*a* that inclines in the pulling out direction. By so doing, the lower rib 58 climbs over the outer peripheral portion of the cap 30, and the protector 14 becomes tiltable with respect to the needle hub 18. For example, the initial contact position of the proximal end side end face 58*a* of the lower rib 58 with the flange-shaped portion 33 may be a position somewhat distant from the groove opening of the accommodating groove 40 toward the groove bottom side. That is, the lower rib 58 may extend toward the opening side of the accommodating groove 40 beyond the contact position with the flange-shaped portion 33 due to the pulling out of the cap 30.

By further pulling out the cap 30 in such a state, the protector 14 tilts along the inclination of the reinforcing rib 52, that is, the protector 14 tilts in the direction separating from the puncture needle 12 (the cap 30) (in the direction of the white arrow in FIG. 3) while gradually increasing the contact area between the flange-shaped portion 33 and the proximal end side end face 58*a* of the lower rib 58. That is, even after the cap 30 has moved to the distal end side and the protector 14 has tilted, the contact state between the flange-shaped portion 33 and the lower rib 58 is maintained in a moving region having a predetermined length in the pulling out direction of the cap 30. As a result, the operating force in the pulling out direction exerted on the cap 30 is converted into an external force in the tilting direction of the protector 14, and the protector 14 stands up so as to be lifted. At the time of the situation in FIG. 3, the reinforcing rib 52 extends in a direction approximately orthogonal to the axial direction, and the contact area between the flange-shaped portion 33 and the proximal end side end face 58*a* of the lower rib 58 becomes maximum. In the present practical embodiment, the inclined portion 60*c* is provided on the proximal end side of the upper edge (the lower edge of the through hole 54) of the lower rib 58. Thus, the area of the proximal end side end face 58*a* of the lower rib 58 is increased by the amount of the inclined portion 60*c*, so as to come into contact with the flange-shaped portion 33 with a wider area. With this configuration, the operating force in the pulling out direction exerted on the cap 30 is easily transmitted to the protector 14.

Of course, as will be described later, the displacement of the protector 14 is performed as a series of operations, and the contact between the flange-shaped portion 33 and the proximal end side end face 58*a* of the lower rib 58, the gradual increase in the contact area, and the like are momentary. Further, in the unused state, even if the reinforcing rib 52 (the proximal end side end face 58*a*) is not inclined with respect to the pulling out direction of the cap 30 (namely, even if the contact area does not gradually increase or the like), by pulling out the protector 14 vigorously, the operating force in the pulling out direction of the cap 30 is exerted on the protector 14 by the momentary contact between the flange-shaped portion 33 and the lower rib 58, and the tilt displacement of the protector 14 can be achieved.

Subsequently, the cap 30 is further pulled out outward in the axial direction, and the operating force (the pulling out force) in the pulling out direction exerted from the flange-shaped portion 33 to the lower rib 58 exceeds the force required for elastically deforming the urging arm 50. As a result, the urging arm 50 is elastically deformed due to the cap 30 being pulled out, and as shown in FIGS. 4 and 5, the protector 14 is automatically displaced and positioned to a second stable position (S2) serving as a puncture position which is away from the puncture needle 12. That is, in the present practical embodiment, a positioning mechanism for positioning the protector 14 at the puncture position (S2) is constituted particularly by the urging arm 50 of the hinge portion 38. In other words, one of the plurality of stable positions of the protector 14 at which the protector 14 is selectively positioned by elastically deforming the urging arm 50 is the puncture position (the second stable position S2). The tilt angle of the length direction of the protector 14 with respect to the axial direction at the second stable position (S2) is not limited, but is set in the range of, for example, 100 degrees to 150 degrees.

The displacement of the protector 14 from the tilt position (N) to the puncture position (S2) in the unused state as described above is performed as a series of operations, and the state shown in FIG. 3 is momentary. However, it is illustrated in order to explain the engagement state between the flange-shaped portion 33 and the lower rib 58 in an easy-to-understand manner. Further, in the present practical embodiment, the maximum protruding portion 29 of the needle hub 18 and the surmountable protrusion 31 of the cap 30 are engaged. Thus, in order to pull out the cap 30 from the needle hub 18, an operating force sufficient for the surmountable protrusion 31 to climb over the maximum protruding portion 29 is required. That is, it is easy to obtain an operating force for pulling out the cap 30 vigorously from the needle hub 18 to displace the protector 14 from the tilt position (N) in the unused state to the puncture position (S2), and the displacement from the tilt position (N) in the unused state to the puncture position (S2) is easily performed more stably and as a series of operations.

Then, the cap 30 can be removed by pulling it outward in the axial direction when the engagement between the flange-shaped portion 33 and the lower rib 58 is released. By the cap 30 being pulled out from the needle hub 18 toward the distal end side to expose the needle tip 16 of the puncture needle 12, the puncture needle 12 can be stuck to the patient. Then, by operating the syringe 24 after puncture of the puncture needle 12, the drug solution in the syringe 24 can be injected into the patient.

Figure 6:
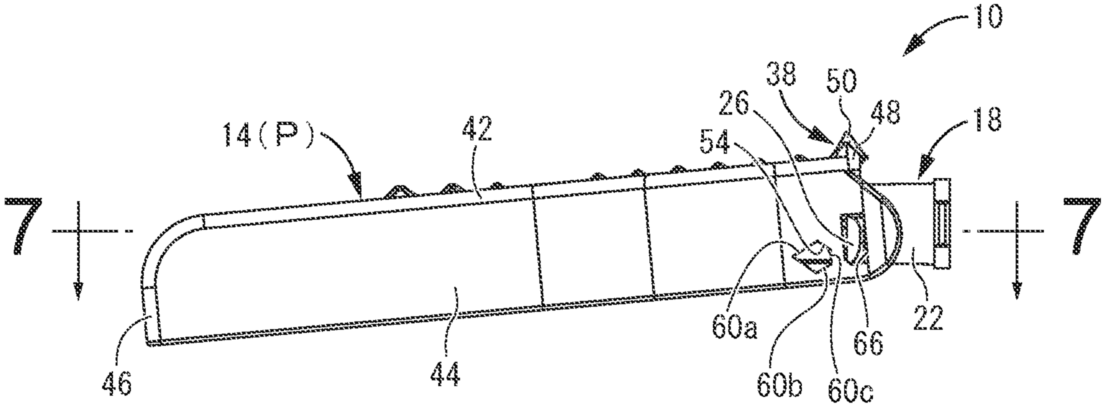
FIG. 6 is a front view showing a state in which the protector is in a protection position in the protector-attached puncture needle shown in FIG. 1.

After using the puncture needle 12, i.e. after removing the puncture needle 12 from the patient, the puncture needle 12 after puncture can be covered and protected by the protector 14. That is, the protector 14 is displaced from the second stable position (S2) shown in FIGS. 4 and 5 to the first stable position (S1) indicated by the chain double-dashed line by catching the distal end portion of the protector 14 by the finger and operating so as to press it out to elastically deform the urging arm 50. Subsequently, by pressing the protector 14 toward the puncture needle 12, the protector 14 undergoes tilt displacement to a protection position (P) shown in FIGS. 6 and 7, and the puncture needle 12 is accommodated in the accommodating groove 40 from the lateral side and protected.

In the present practical embodiment, the locking portion 64 that projects from the end of the second reinforcing rib 62 on the groove opening side toward the groove bottom portion is provided, and by the puncture needle 12 climbing over the locking portion 64 and being locked to the said locking portion 64, the protector 14 is prevented from displacing in the direction separating from the puncture needle 12 to re-expose the puncture needle 12.

In particular, in the present practical embodiment, the locking protrusions 26, 26 project from the needle hub 18 to diametrically both sides, and the locking holes 66, 66 are provided at the proximal end portions of the pair of side walls 44, 44. In the protected state of the puncture needle 12 shown in FIGS. 6 and 7, the locking protrusions 26, 26 can be locked in the locking holes 66, 66. That is, in the present practical embodiment, the positioning mechanism for positioning the protector 14 at the protection position (P) is constituted by at least one of the locking of the puncture needle 12 to the locking portion 64 and the locking of the locking protrusions 26, 26 to the locking holes 66, 66.

In the protector-attached puncture needle 10 of the present practical embodiment having the above structure, the reinforcing ribs 52, 52 and the second reinforcing ribs 62, 62 are provided on the inner surfaces of the side walls 44, 44 of the protector 14. Thus, the strength and the rigidity are improved, thereby effectively preventing deformation such as collapse of the side walls 44, 44 in the direction of approaching each other. In particular, since the reinforcing ribs 52, 62 on the inner surface of the side wall 44 of the protector 14 are provided so as to continuously extend from the inner surface of the bottom wall 42 to the side wall 44, the connecting corner between the bottom wall 42 and the side wall 44 where the maximum moment is generated when an external force such as the collapse of the side wall 44 acts is also efficiently reinforced by the reinforcing rib 52. As a result, while adopting the relatively thin side wall 44, the reinforcing rib 52 can efficiently secure the deformation strength and prevent the problem of deformation of the protector 14 at the time of storage or the like.

Further, since diametrically both sides of the outer peripheral portion of the cap 30 enter the through holes 54, 54, an outward expanding force in the direction of opposition is prevented from being exerted on the side walls 44, 44 due to the contact reaction force with the outer peripheral portion of the cap 30, thereby suppressing the outward deformation of the side walls 44, 44. As a result, even when the protector-attached puncture needle 10 is stored for a long period of time in the unused state shown in FIGS. 1 and 2, the side walls 44, 44 do not have a peculiarity of spreading outward. Thus, in the protected state of the puncture needle 12, the puncture needle 12 can be more stably protected by more reliably preventing release of locking of the puncture needle 12 by the locking portion 64 and the locking of the locking protrusion 26 to locking hole 66.

Besides, by forming the through holes 54, 54 in the side walls 44, 44, it becomes easy to form a recess on the inner surface of the side walls 44, 44 by molding or the like. Further, as compared with the case where a recess is formed in an undercut manner on the inner surface of the side wall, for example, a corner portion can be formed more reliably at the opening edge of the through holes 54, 54, and the locking to the outer peripheral surface of the cap 30 due to the opening edges of the through holes 54, 54 can be stably realized.

Furthermore, in the present practical embodiment, since the protector 14 displaces from the tilt position (N) in the unused state to the puncture position (the second stable position S2) approximately at the same time as the cap 30 is pulled out, This makes it possible to avoid the complicated operation of removing the cap 30 after displacing the protector 14 to the puncture position (S2). In particular, in the present practical embodiment, it is necessary for the surmountable protrusion 31 to climb over the maximum protruding portion 29 when pulling out the cap 30 from the needle hub 18, and the tilting of the protector 14 can be performed as a series of operations by skillfully utilizing the operating force required for the climbing over. Further, by adopting a spring hinge (particularly the urging arm 50 of the hinge portion 38) as the positioning mechanism, it is possible to easily set the first stable position (S1) and the second stable position (S2).

Further, in the present practical embodiment, in the state in which the tilt position (N) of the protector 14 is held when not in use, the end of the second reinforcing rib 62 on the groove opening side is in contact with the outer peripheral portion of the cap 30. With this configuration, even if an external force is applied to the protector 14 in the direction of approaching the puncture needle 12, the displacement of the protector 14 is limited, thereby avoiding damage to the puncture needle 12 or the like due to the excessive displacement of the protector 14.

Furthermore, in the present practical embodiment, the cap 30 has an approximately cylindrical shape and the outer peripheral portion of the cap 30 enters the through holes 54, 54. Thus, it is unnecessary to position the cap 30 and the protector 14 in the circumferential direction, thereby easily holding the tilt position (N) of the protector 14 in the unused state. Besides, since the outer peripheral protrusion at the proximal end side opening portion of the cap 30 comprises the flange-shaped portion 33 over the entire circumference as well, the engagement with the engaging rib (the lower rib 58) can be achieved without performing positioning in the circumferential direction. Further, since the engaging ribs (the reinforcing ribs 52) are provided on both sides of the accommodating groove 40, the operating force in the pulling out direction is stably transmitted from the flange-shaped portion 33 to the lower rib 58, thereby more reliably realizing the displacement of the protector 14 to the puncture position (S2).

In particular, in the present practical embodiment, since the upper edges 60*a* of the through holes 54, 54 and the parallel portions 60*b* at the lower edges thereof, which are the contact portions between the cap 30 and the protector 14, extend approximately parallel to the central axis of the cap 30, the cap 30 and the protector 14 come into approximately linear contact with each other. Thus, for example, in comparison with the case of point contact, larger length dimensions of the contact portions 60*a*, 60*b* can be secured, thereby more stably exhibiting the holding effect of the protector 14. Note that by providing the inclined portion 60*c* on the proximal end side of the lower edge of the through hole 54, the area of the proximal end side end face 58*a* in the lower rib 58 can be increased, so that the protector 14 can be more stably displaced to the puncture position (S2) due to increase in the contact area between the flange-shaped portion 33 and the proximal end side end face 58*a*.

Furthermore, in the present practical embodiment, in the protected state of the puncture needle 12, the locking protrusions 26, 26 are locked in the locking holes 66, 66, thereby preventing the protector 14 from accidentally displacing in the direction of separating from the puncture needle 12. Therefore, re-exposure of the puncture needle 12 after use can be more reliably avoided.

Although the practical embodiment of the present invention has been described above, the present invention is not limitedly interpreted based on the specific description in the practical embodiment, but may be embodied with various changes, modifications and improvements which may occur to those skilled in the art.

For example, in the above-described practical embodiment, the recess opened in the inner surface of the side wall 44 of the accommodating groove 40 is formed by the through hole 54 penetrating the side wall 44 in the thickness direction, but the recess may be a bottomed recess. Alternatively, a relative recess may be formed by providing a plurality of convex portions on the inner surface of the side wall, and the first and second positioning protrusions may be formed by these convex portions.

Furthermore, the reinforcing ribs are not essential in the present invention. It would also be acceptable to, for example, form a recess (or a through hole) on the inner surface of the side wall where the reinforcing rib is not provided so that the outer peripheral portion of the cap enters the said recess. However, in the present invention, the means for holding the tilt position of the protector in the unused state is not limited to the mode described in the above practical embodiment, and the recess (or the through hole) provided on the inner surface of the side wall of the accommodating groove and the first and second positioning protrusions are not essential.

Further, in the above-described practical embodiment, diametrically both sides of the outer peripheral portion of the cap 30 enter the through hole 54 and are locked by being sandwiched between the upper rib 56 (the first positioning protrusion) and the lower rib 58 (the second positioning protrusion) from above and below. However, the component for locking the outer peripheral portion of the cap is not limited to the upper rib and the lower rib. That is, it would also be acceptable that the lower rib comes into contact with the outer peripheral portion of the cap from below, while the groove opening side end of the second reinforcing rib comes into contact with the outer peripheral portion of the cap, so as to hold the tilt position of the protector. Therefore, the upper rib is not essential in the present invention, and when the upper rib is not provided, the first positioning protrusion may be formed by the second reinforcing rib. In this way, the first positioning protrusion and the second positioning protrusion may be separated from each other relatively largely in the axial direction.

Besides, the specific shape of the reinforcing rib is not limited. For example, the protrusion dimension and the rib width dimension may vary in the length direction, and it is also possible to adopt the reinforcing rib extending in a bent or curved shape instead of a linear shape, or the like.

Furthermore, in the above-described practical embodiment, the cap 30 has an approximately cylindrical shape overall, but the shape of the cap is not limited. The cap may have, for example, a polygonal tubular shape, and may be configured such that the apex portion (the corner portion) enters the recess (the through hole) and is locked.

In the present invention, in the state in which the outer peripheral portion of the cap enters the recess (including the through hole) and is locked, it is preferable that the contact reaction force with the cap is not applied to the side wall. However, midway during the cap entering the accommodating groove, the contact reaction force may be applied to the side wall, and the side wall may deform outward in the direction of opposition, for example. Indeed, the contact reaction force with the cap may be applied to the side wall in the state in which the outer peripheral portion of the cap enters the recess and is locked.

Further, in the above-described practical embodiment, the protector 14 is integrally molded with the needle hub 18, but the protector may be separated from the needle hub and attached later. The protector and the needle hub do not need to be connected by a spring hinge (the hinge portion 38) as in the above practical embodiment. That is, the protector and the needle hub may be connected by, for example, an elastically deformable plate-shaped member (an elastic hinge), the protector may be tiltable with respect to the needle hub by the said plate-shaped member (the elastic hinge) being deformed to curve or the like. In this case, the stable position of the protector set by the elastic hinge may be only the puncture position (S2) away from the puncture needle, and in the unused state, the protector is held at the tilt position (N) where the elastic hinge is elastically deformed so as to approach the cap. Meanwhile, when used, by removing the cap, the protector may automatically displace to the puncture position (S2) according to the elastic recovering action of the elastic hinge. In particular, in such a case, it is sufficient that the protector is prevented from displacing to the puncture position (S2) and is held at the approaching position (N) to the cap in the unused state. Such a mode can be realized by, for example, providing the lower rib 58 (the second positioning protrusion) in the above practical embodiment and locking it to the outer peripheral surface of the cap. That is, in this mode, the upper rib 56 (the first positioning protrusion) is not essential.

Alternatively, the protector and the needle hub may be connected by a pin or the like so that the protector is tiltable with respect to the needle hub by using the said pin or the like as a rotation axis, or a leaf spring or a coil may be applied as a spring action as needed. Therefore, the urging arm is not essential in the hinge portion, and the first stable position and the second stable position set by the urging arm are not essential either. Alternatively, even when a plurality of stable positions are set by the urging arm, two or more stable positions may be set. That is, in the present invention, the mode in which that the protector automatically displaces from the tilt position in the unused state to the puncture position approximately at the same time as the removal of the cap is not essential, and the pulling out of the cap may be performed after separating the protector in the tilting direction.

Moreover, in the above-described practical embodiment, the surmountable protrusion 31 of the cap 30 is engaged by climbing over the maximum protruding portion 29 of the needle hub 18, thereby making it easy to obtain an operating force in the pulling out direction of the cap 30 from the needle hub 18. However, the engagement mode between the needle hub and the cap is not limited to this mode. That is, it would also be acceptable to provide concave and convex portions fitted with each other between the needle hub and the cap, and by using the operating force of pulling out the cap from the needle hub to release the concave and convex fitting, the tilt position of the protector is configured to automatically displace from the unused state (N) to the puncture position (S2).

KEYS TO SYMBOLS

10 protector-attached puncture needle
12 puncture needle
14 protector
16 needle tip
18 needle hub
20 small-diameter tubular portion
22 large-diameter tubular portion
24 syringe
26 locking protrusion (positioning mechanism)
28 fixing plate portion
29 maximum protruding portion
30 cap
31 surmountable protrusion
32 ridge
33 flange-shaped portion (contact protrusion)
34 connecting portion
38 hinge portion (positioning mechanism)
40 accommodating groove
42 bottom wall
44 side wall
46 distal end side wall
48 connecting arm
50 urging arm (positioning mechanism, elastic hinge)
52 reinforcing rib (engaging rib)
54 through hole (recess)
56 upper rib (first positioning protrusion)
58 lower rib (second positioning protrusion)
58*a* proximal end side end face
60*a* upper edge of through hole (lower edge of upper rib, contact portion)
60*b* parallel portion (contact portion)
60*c* inclined portion
62 second reinforcing rib
64 locking portion (positioning mechanism)
66 locking hole (positioning mechanism)

The invention claimed is:

1. A protector-attached puncture needle comprising:
a puncture needle;
a cap removably covering the puncture needle before use; and
a protector configured to cover the puncture needle after use, wherein
the protector is tiltably supported by a needle hub of the puncture needle, and the protector includes an accommodating groove that opens toward the puncture needle in a tilting direction to accommodate the puncture needle, inner surfaces of both side walls of the accommodating groove of the protector include respective reinforcing ribs extending from a groove bottom portion toward a groove opening side, the reinforcing ribs include respective through holes each opening on the inner surface and an outer surface of the corresponding side wall, and diametrically both sides of an outer peripheral portion of the cap enter and are locked in the respective through holes of the reinforcing ribs such that a tilt position of the protector in an unused state before removal of the cap is held, the respective reinforcing ribs provided on both side walls of the protector extend so as to be inclined in a length direction of the protector, each reinforcing rib is divided by the through hole into an upper rib disposed above the through hole and a lower rib disposed below the through hole, the diametrically both sides of the outer peripheral portion of the cap are disposed and positioned between the respective upper ribs and the respective lower ribs, the protector includes second reinforcing ribs positioned on a distal end side with respect to the reinforcing ribs and extending from the groove bottom portion toward the groove opening side on the respective inner surfaces of the side walls of the accommodating groove, and an end of each second reinforcing rib on the groove opening side is in contact with the outer peripheral portion of the cap such that in the unused state before removal of the cap, tilt of the protector in a direction approaching the puncture needle is limited.

2. A protector-attached puncture needle comprising:

a puncture needle;

a cap removably covering the puncture needle before use; and a protector configured to cover the puncture needle after use, wherein the protector is tiltably supported by a needle hub of the puncture needle, and the protector includes an accommodating groove that opens toward the puncture needle in a tilting direction to accommodate the puncture needle, inner surfaces of both side walls of the accommodating groove of the protector include respective first positioning protrusions and respective second positioning protrusions that are separated from each other in the tilting direction of the protector, diametrically both sides of an outer peripheral portion of the cap, the cap being inserted in the accommodating groove, are positioned between the respective first positioning protrusions and the respective second positioning protrusions such that a tilt position of the protector in an unused state before removal of the cap is held in a state in which an expanding force is not exerted on the accommodating groove, the expanding force being caused by contact reaction force of the side walls of the accommodating groove of the protector with respect to the diametrically both sides of the outer peripheral portion of the cap inserted in the accommodating groove, the protector includes first reinforcing ribs and second reinforcing ribs positioned on a distal end side with respect to the first reinforcing ribs and extending from a groove bottom portion toward a groove opening side on the respective inner surfaces of the side walls of the accommodating groove, and an end of each second reinforcing rib on the groove opening side is in contact with the outer peripheral portion of the cap such that in the unused state before removal of the cap, tilt of the protector in a direction approaching the puncture needle is limited.

3. The protector-attached puncture needle according to claim 1, wherein the outer peripheral portion of the cap inserted in the accommodating groove of the protector has a cylindrical shape.

4. A protector attached puncture needle comprising:

a puncture needle;

a cap removably covering the puncture needle before use; and a protector configured to cover the puncture needle after use, wherein the protector is tiltably supported by a needle hub of the puncture needle, and the protector includes an accommodating groove that opens toward the puncture needle in a tilting direction to accommodate the puncture needle, inner surfaces of both side walls of the accommodating groove of the protector include respective reinforcing ribs extending from a groove bottom portion toward a groove opening side, the reinforcing ribs include respective through holes each opening on the inner surface and an outer surface of the corresponding side wall, and diametrically both sides of an outer peripheral portion of the cap enter and are locked in the respective through holes of the reinforcing ribs such that a tilt position of the protector in an unused state before removal of the cap is held, the respective reinforcing ribs provided on the both side walls of the protector extend so as to be inclined in a length direction of the protector, each reinforcing rib is divided by the through hole into an upper rib disposed above the through hole and a lower rib disposed below the through hole, the diametrically both sides of the outer peripheral portion of the cap are disposed and positioned between the respective upper ribs and the respective lower ribs, the protector includes a pair of contact portions that are in contact with the outer peripheral portion of the cap, the contact portions extending parallel to a center axis of the cap while being separated from each other in the tilting direction at the tilt position of the protector in the unused state before removal of the cap, and the outer peripheral portion of the cap enters between the contact portions such that the tilt position of the protector is held.

5. The protector-attached puncture needle according to claim 1, further comprising a positioning mechanism positioning the tilt position of the protector separately at a puncture position away from the puncture needle and at a protection position where the puncture needle is covered.

6. A protector-attached puncture needle comprising:

a puncture needle;

a cap covering the puncture needle before use and capable of being pulled out; and a protector being tiltable and configured to cover the puncture needle from a lateral side after use, wherein the cap includes a contact protrusion configured to come into contact with the protector when the cap is pulled out, the protector being held at a tilt position approaching the cap before use, as the cap is pulled out, the contact protrusion comes into contact with the protector and exerts a pulling out force so as to tilt the protector to a tilt position away from the cap, the protector includes an accommodating groove configured to accommodate and cover the puncture needle from the lateral side after use, an engaging protrusion projects on at least one of inner surfaces of side walls of the accommodating groove, the engaging protrusion being configured to be contacted by the contact protrusion due to pulling out of the cap, at the position approaching the cap where the protector is held before use, the engaging protrusion of the protector extends toward an opening side of the accommodating groove beyond a contact position with the contact protrusion due to pulling out of the cap, and even after the cap starts to move due to pulling out operation and the protector starts to tilt, the contact protrusion is configured to be in contact with the engaging protrusion in a moving region having a predetermined length in a pulling out direction of the cap.

7. The protector-attached puncture needle according to claim 6, wherein the protector is connected to a needle hub of the puncture needle by an elastic hinge by which a puncture position away from the puncture needle is set as a stable position.

8. The protector-attached puncture needle according to claim 6, wherein the contact protrusion of the cap is constituted by a flange-shaped portion projecting on an outer peripheral surface on a proximal end side of the cap.

9. The protector-attached puncture needle according to claim 1, wherein a lower edge of the upper rib, which is an upper edge of the through hole, constitutes an end face extending in an intersecting direction that intersects with an inclination direction of the reinforcing rib, and an upper edge of the lower rib, which is a lower edge of the through hole, includes an end face extending in the intersecting direction.

10. The protector-attached puncture needle according to claim 9, wherein an inclined portion that inclines to a side of the upper edge of the through hole is provided on a proximal end side of the upper edge of the lower rib.

11. The protector-attached puncture needle according to claim 6, wherein the protector has a contact target part configured to be contacted by the contact protrusion due to pulling out of the cap, and the contact target part has a shape by which an operating force in a pulling out direction of the cap is converted into an external force in a tilting direction separating the protector from the cap.

* * * * *